United States Patent
James

(10) Patent No.: US 11,565,072 B2
(45) Date of Patent: Jan. 31, 2023

(54) ASSISTED WALKING DEVICE AND METHOD OF USE

(71) Applicant: Jeffrey L. James, Oklahoma City, OK (US)

(72) Inventor: Jeffrey L. James, Oklahoma City, OK (US)

( * ) Notice: Subject to any disclaimer, the term of this patent is extended or adjusted under 35 U.S.C. 154(b) by 349 days.

(21) Appl. No.: 16/830,007

(22) Filed: Mar. 25, 2020

(65) Prior Publication Data

US 2021/0299391 A1  Sep. 30, 2021

(51) Int. Cl.
*A61M 16/10* (2006.01)
*A61H 3/04* (2006.01)

(52) U.S. Cl.
CPC .............. *A61M 16/101* (2014.02); *A61H 3/04* (2013.01); *A61H 2201/107* (2013.01)

(58) Field of Classification Search
CPC ............ A61M 16/101; A61M 16/0063; A61M 16/024; A61M 2205/3553; A61M 2205/3584; A61M 2205/3592; A61M 2205/505; A61M 2205/52; A61M 2205/586; A61M 2205/8206; A61M 2230/06; A61M 2230/30; A61H 3/04; A61H 2201/107; A61H 2201/0192; A61H 2201/1635; A61H 2201/5046; B01D 53/0407; B01D 2253/108; B01D 2257/102; B01D 2259/4533
See application file for complete search history.

(56) References Cited

U.S. PATENT DOCUMENTS

| | | | |
|---|---|---|---|
| 4,251,044 A | 2/1981 | Olson | |
| 6,453,920 B1* | 9/2002 | Izuchukwu | F17C 1/04 222/206 |
| 6,478,850 B2 | 11/2002 | Warren | |
| 6,672,321 B2 | 1/2004 | Hamilton | |
| 6,764,534 B2 | 7/2004 | McCombs et al. | |
| 7,935,030 B1 | 5/2011 | Nesbitt | |
| 8,016,925 B2 | 9/2011 | McCombs et al. | |
| 8,256,415 B2 | 9/2012 | Hughes et al. | |
| 9,199,055 B2 | 12/2015 | Galbraith et al. | |
| 9,649,243 B2 | 5/2017 | Johnson et al. | |
| 9,974,919 B2 | 5/2018 | Richard et al. | |
| 2003/0005928 A1* | 1/2003 | Appel | B01D 53/0446 128/202.26 |

(Continued)

*Primary Examiner* — Timothy A Stanis
*Assistant Examiner* — Matthew R Moon
(74) *Attorney, Agent, or Firm* — D. Ward Hobson

(57) ABSTRACT

The inventive concepts disclosed and claimed herein are generally directed to an improved assisted walking device, such as a cane, walker or wheelchair, that includes an integrated oxygen concentrator housed within the assisted walking device. In some embodiments, for example, the improved assisted walking device includes a handle, a control pad, an elongated housing having an interior chamber, an oxygen concentrator, a leg member and a foot member. The oxygen concentrator detachably positioned within the interior chamber of the elongated housing and including an adsorption system configured to generate a flow of oxygen enriched gas, a compressor that includes a motor, a battery, a plurality of sieve beds configured to extract oxygen-enriched gas from ambient air, and a controller in communication with the control pad.

5 Claims, 3 Drawing Sheets

(56) References Cited

U.S. PATENT DOCUMENTS

| | | | | |
|---|---|---|---|---|
| 2005/0076939 A1* | 4/2005 | Karasin | .................... | A61H 3/04 |
| | | | | 135/67 |
| 2007/0000531 A1* | 1/2007 | Russo | ...................... | A61H 3/02 |
| | | | | 135/910 |
| 2017/0319802 A1* | 11/2017 | Holder | .............. | A61M 16/0672 |
| 2018/0133094 A1* | 5/2018 | Helfer | ...................... | A61H 3/04 |

* cited by examiner

ASSISTED WALKING DEVICE AND METHOD OF USE

FIELD OF INVENTION

The invention is in the technical field of assisted walking devices and portable oxygen concentrators for therapeutic use. In particular, the invention is generally directed to a novel assisted walking device that include an integrated oxygen concentrator for therapeutic use as described and claimed herein.

BACKGROUND

People with breathing conditions, including but not limited to, asthma, chronic obstructive pulmonary disease (COPD), chronic bronchitis, emphysema, lung cancer, cystic fibrosis, or pneumonia, for example, often require additional oxygen for breathing. In addition, many people who have breathing conditions also have limited mobility and require use of an assisted walking device, such as a cane, wheelchair, or walker, for example.

To treat a breathing condition, a physician may prescribe use of an oxygen concentrator. An oxygen concentrator is a medical device configured for delivering doses or a continuous stream of oxygen to a patient in need of additional oxygen. Traditional oxygen concentrators work by filtering the surrounding air, compressing it to the required density and then delivering the concentrated oxygen into a dose delivery system or continuous stream to the person. An oxygen concentrator has a compressing element but operates in a different manner from a traditional oxygen tank that supplies compressed oxygen. The compressed oxygen inside an oxygen tank, for example, is a set amount of oxygen that is dispensed to the user, eventually requiring a refill or replacement when the oxygen inside the tank runs out. People using compressed oxygen tanks must keep several tanks on hand to ensure that they do not run out of oxygen before receiving a refill. An oxygen concentrator, on the other hand, is an oxygen machine that pulls in air from the atmosphere, purifies it, compresses it and then delivers the oxygen-rich air continuously to the user. Traditional oxygen concentrators may be configured to be fixed in a stationary position, such as in a home or alternatively, may be configured to be portable such that a person may carry the traditional oxygen concentrator with them, for example.

Unfortunately, however, traditional oxygen concentrators, even so-called portable oxygen concentrators, are not configured for use by persons who also require assistive walking devices. Most traditional oxygen concentrators are bulky, require access to a back-up power source for additional safety (in addition to a battery) and may include a variety of oxygen hoses and electrical cords configured to ensure continuous and uninterrupted delivery of oxygen. For example, carrying a traditional oxygen concentrator or attaching it to a traditional assisted walking device alters the weight distribution of the traditional walking device making walking more difficult and increasing the likelihood that a person may fall and become injured. Thus, making use of traditional oxygen concentrators, even portable oxygen concentrators, in combination with traditional assisted walking devices cumbersome and dangerous.

Additional disadvantages associated with use of traditional assistive walking devices and traditional oxygen concentrators include, but are not limited to, unnecessary oxygen tanks and hoses, difficulty using both device simultaneously, and a tendency for people to lean forward while using traditional assisted walking devices, causing the added weight associated with a traditional oxygen concentrator to pull the person forward, which further increases the effects of gravity on posture, particularly in elderly persons. Such improper posture, over time, can cause wedging of degenerative discs. Wedging of the discs posteriorly towards the spinal cord can cause harm, including osteoporosis and spinal compression fractures, for example. Persons carrying traditional oxygen concentrators also tend to self-correct the extra weight being carried, causing distortions in balance and increasing the likelihood of falls, when not using the assisted walking device, which may cause injury or death. These issues can be further complicated by a variety of other medical conditions and medications.

To improve the usefulness and safety of traditional assisted walking devices used by people who are also in need of oxygen, it would be advantageous to provide an improved assisted walking device that includes an integrated oxygen concentrator housed within the assisted walking device, as disclosed and claimed herein.

SUMMARY OF THE INVENTION

The inventive concepts disclosed and claimed herein are generally directed to an improved assisted walking device, such as a cane, walker or wheelchair, that includes an integrated oxygen concentrator housed within the assisted walking device. In some embodiments, the improved assisted walking device generally includes a handle, an elongated housing, an oxygen concentrator, a leg member and a foot member. The handle having a control pad, a top end, an ergonomic grip, and a bottom end. The elongated housing having a top end, a bottom end, and an opening into an interior chamber. The interior chamber extending between the top end and the bottom end of the elongated housing. The interior chamber having an upper shelf and a lower shelf positioned therein. The top end of the elongated housing detachably connected to the bottom end of the handle. The oxygen concentrator detachably positioned within the interior chamber of the elongated housing and detachably secured by the upper shelf and lower shelf of the interior chamber of the elongated housing.

The oxygen concentrator including an adsorption system configured to generate a flow of oxygen enriched gas, a compressor that includes a motor, a plurality of sieve beds configured to extract oxygen-enriched gas from ambient air, a controller in communication with the control pad positioned on the handle and a battery. The leg member having a top end and a bottom end. The top end of the leg member detachably connected to the bottom end of the elongated housing. The foot member having a top end and a bottom end. The top end of the foot member detachably connected to the bottom end of the leg member. The bottom end of the foot member for contacting the ground surface.

In some embodiments, the control pad of the improved assisted walking device further includes a touch screen configured to permit a user to operate the oxygen concentrator directly from the handle. While in other embodiments, the control pad may be located on the elongated housing or elsewhere on the assisted walking device, for example. Further, in some embodiments, the oxygen concentrator is configured to be replaceable, such that the oxygen concentrator may be selectively inserted and selectively removed from the assisted walking device through the opening in the elongated housing. While in some embodiments, the sieve beds and the battery of the oxygen concentrator are also configured to be replaceable, such that the sieve beds and the battery may be selectively inserted and selectively removed from the oxygen concentrator.

Further, in some embodiments, the improved assisted walking device may include a plurality of foot members and include additional bracing structures configured to stabilize the assisted walking device. For example, in some embodiments, the assisted walking device may contain a single leg member and foot member, similar to a cane, while in other embodiments, the assisted walking device may contain four leg members and four foot members, similar to a walker, for example, while in other embodiments the assisted walking device may include wheels. In this way, the assisted walking device may be configured to be used as part of a system of component parts that may be interchanged, reused, or modified to accommodate various heights, weights and walking abilities and for a variety of different therapeutic purposes.

The improved assisted walking device provides numerous advantages over traditional assisted walking devices and traditional oxygen concentrators. The improved assisted walking device is a more efficient therapeutic device, capable of being used as a system with various component parts capable of use by many different persons and for many different therapeutic purposes. The assisted walking device is configured to be battery operated and rechargeable. Further the improved assisted walking device increases mobility, reducing healthcare costs associated with multiple devices, and increases the overall health and wellness of persons using the improved assisted walking device. The improved assisted walking device further helps to reduce falls and maintain oxygen saturation levels, is less embarrassing to a person than carrying a bulky and more visible oxygen concentrator, increases health by encouraging walking, permits a user to multi-task and use their hands for tasks other than carrying a separate oxygen concentrator, does not off-set a person's center of gravity, does not impair posture or cause sacral or spinal torsions, prevents possible spinal fractures for persons with osteoporosis or cancer, is easy to use, reduces the number of devices a person that may be suffering from dementia may have to remember, improves transfer of persons in and out of vehicles, is more efficient at navigating curbs and other street impediments, simplifies public restroom use by persons, reduces cost, improves gait pattern and walking ability, increases freedom of movement, and is more efficient in confined or small spaces, for example.

The improved assisted walking device is configured to help prolong life expectancy and improve health of persons. The assisted walking device expands the base of support for the person and is capable of transitioning gait cycle from a bi-pedal mode to a tri-pedal mode or quad-pedal mode as needed. The assisted walking device offloads body weight from injured or degenerative lower extremities and helps prevent falls by improving proper gait pattern. The assisted walking device also delivers pulsed or continuous supplemental oxygen to the person, as prescribed by licensed medical professionals.

It is to such an improved assisted walking device and methods of use thereof that exemplary embodiments of the inventive concepts disclosed and claimed herein are directed.

BRIEF DESCRIPTION OF THE SEVERAL VIEWS OF THE DRAWINGS

Like reference numerals in the figures represent and refer to the same or similar element or function. Implementations of the disclosure may be better understood when consideration is given to the following detailed description thereof. Such description makes reference to the annexed pictorial illustrations, schematics, graphs, drawings, and appendices. In the drawings.

DETAILED DESCRIPTION OF EXEMPLARY EMBODIMENTS

Figure 1:
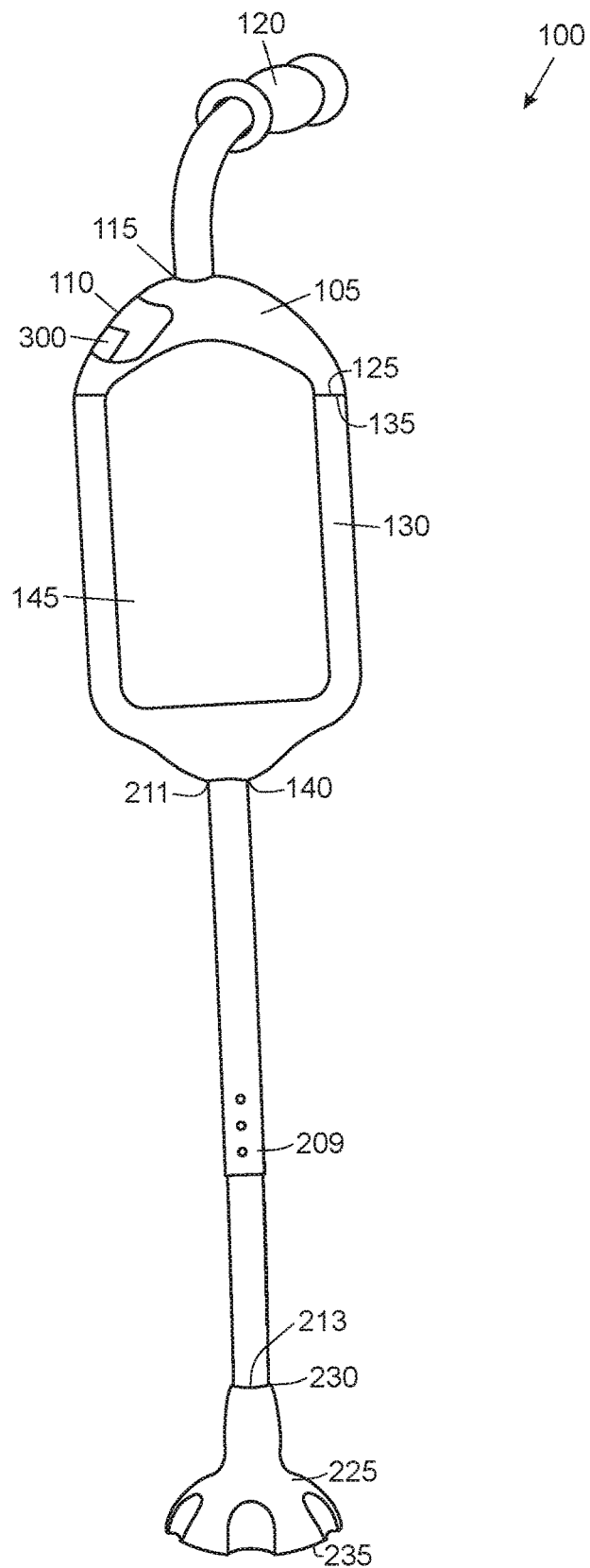
FIG. 1 is a perspective side view of an assisted walking device (100) in accordance with the inventive concepts disclosed herein.

Before explaining at least one embodiment of the inventive concepts disclosed herein in detail, it is to be understood that the inventive concepts are not limited in their application to the details of construction and the arrangements of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

As used herein, the terms "comprises," "comprising," "includes." "including," "has," "having," or any other variation thereof, are intended to cover a non-exclusive inclusion. For example, a system, assembly, method, process, article, or apparatus that comprises a list of elements or steps is not necessarily limited to only those elements or steps but may include other elements and steps not expressly listed.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Figure 2:
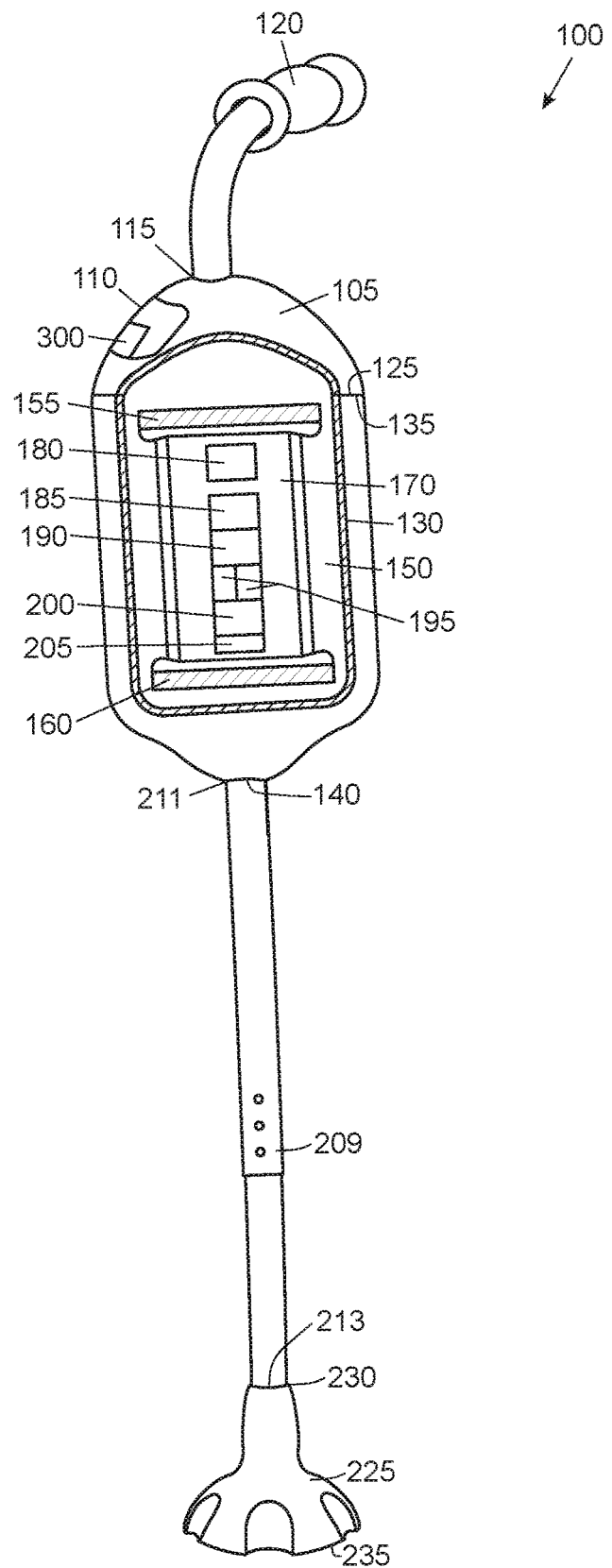
FIG. 2 is a perspective sectional view of an assisted walking device (100) in accordance with the inventive concepts disclosed herein.

Referring now to FIGS. 1-2, shown therein is a perspective view of an embodiment of an assisted walking device (100) in accordance with the inventive concepts disclosed herein. The assisted walking device (100) includes a handle (105). The handle (105) having a control pad (110), a top end (115), an ergonomic grip (120), and a bottom end (125). The assisted walking device (100) further including an elongated housing (130). The elongated housing (130) having a top end (135), a bottom end (140), and an opening (145) into an interior chamber (150). The interior chamber (150) extending between the top end (135) and the bottom end (140) of the elongated housing (130). The interior chamber (150) having an upper shelf (155) and a lower shelf (160) positioned therein. The top end (135) of the elongated housing (130) detachably connected to the bottom end (140) of the handle (105).

The assistive walking device (100) further including an oxygen concentrator (170). The oxygen concentrator (170) detachably positioned within the interior chamber (150) of the elongated housing (130) and detachably secured by the upper shelf (155) and lower shelf (160) of the interior chamber (150) of the elongated housing (130). The oxygen concentrator (170) including an adsorption system (180) configured to generate a flow of oxygen enriched gas, a compressor (185) that includes a motor (190), a plurality of sieve beds (195) configured to extract oxygen-enriched gas from ambient air, a controller (200) in communication with the control pad (110) positioned on the handle (105), and a battery (205).

The assisted walking device (100) further includes a leg member (209) for supporting the assisted walking device (100). The leg member (209) having a top end (211) and a bottom end (213). The top end (211) of the leg member (209) detachably connected to the bottom end (140) of the elongated housing (130). The assisted walking device (100) further includes a foot member (225) for stabilizing the assisted walking device (100) on a ground surface. The foot member (225) having a top end (230) and a bottom end (235). The top end (230) of the foot member (225) detachably connected to the bottom end (213) of the leg member (209). The bottom end (235) of the foot member (225) for contacting the ground surface.

As shown therein, the assisted walking device (100) includes a handle (105). The handle (105) having a control pad (110), a top end (115), an ergonomic grip (120) and a bottom end (125). The handle (105) may be constructed from any type of material that is sufficient to function as described and claimed herein. For example, the handle (105) may be constructed from plastics, metals, non-metals, alloys, resins, composite materials, organic compounds, non-organic compounds, papers, fabrics, combinations thereof and the like. The handle (105) may be constructed from a unitary piece of material or alternatively may be constructed from a variety of different materials. The handle (105) may also include reinforcing or bracing structures, such as ribs or struts, for example, or combinations thereof.

Further, the shape of the handle (105) may be any shape, including but not limited to a circular, square or triangular shape for example. The shape of the handle (105) is shown as having a substantially cone shape so as to fit over the top of the elongated housing (130) and be detachably connected thereto, it being understood however, that the shape of the handle (105) may be modified to fit any desired shape, including any desired shape of the elongated housing (130). The handle (105) may be detachably connected to the elongated housing (130) by any means known in the art. For example, screws, snaps, pins, bolts, combinations thereof and the like.

The control pad (110) is configured to be positioned on a top portion of the handle (105) so as to be capable of being viewed and controlled by a user while using the assisted walking device (100). It should be understood however, that the control pad (110) may be located in a variety of locations on the assisted walking device (100), including, but not limited to, being positioned on the elongated housing (130) or on the oxygen concentrator (170), for example. The control pad (100) is a computer or similar electronic device configured for storing, sending, receiving and processing data, according to instructions given to it by a computer program. The control pad (100) may be operated manually by a user using touch controls, or automatically with a variety of pre-set features for automated control. The control pad (110) may be detachably connected to the handle (105) by any means known in the art. For example, screws, snaps, glue, pins, bolts, combinations thereof and the like. The control pad (110) is configured to control the assisted walking device (100), including the oxygen concentrator (170).

In some embodiments, the control pad (110) of the assisted walking device (100) includes a touch screen (300) configured to permit a user to operate the oxygen concentrator (170) by touching the touch screen (300) of the control pad (110). While in some embodiments, the control pad (110) may be configured to be manually operated by pressing buttons, pressing a touch screen (300), video screen, or flipping a switch for example. The control pad (110) may also be configured to permit a user to view data associated with the assisted walking device (100) and data associated with the health of the user. Likewise, the control pad (110) may be configured to automatically operate the oxygen concentrator (170), record data and output data, using a variety of pre-set controls or operations that may be pre-set by a user. Likewise, a user may monitor in real-time operations of the assisted walking device (100) on the control pad, by viewing the control pad (100) and may monitor in real-time user data, such as steps taken by the user and other medical and health data, such as blood pressure, heart rate and other data, for example. Further, the user may monitor in real time data associated with the assisted walking device (100), including stored data and real time data associated with battery life, oxygen concentration, oxygen saturation, oxygen doses, schedules, and other information, reports and summaries, for example. The control pad (100) and controller (200) may each also be configured to output remotely, automatically or upon demand, via a wireless communication, such as a Wi-Fi connection over the internet or private network, for example, to one or more remote computer, various reports, summaries, spreadsheets and data compilations of user health and performance of the assisted walking device (100) for example.

The control pad (110) may be hard-wired to electronically and mechanically control the oxygen concentrator (170) by electronic communication with the controller (200). Alternatively, the control pad (110) may be configured to control the oxygen concentrator (170) electronically through a wireless communications network, such as through radio waves, WiFi, Bluetooth®, and the like, for example. In some embodiments, the control pad (100) may communicate with the controller (200) over the internet, worldwide web, or a local, private or other secure data network. Wireless communications networks are known in the art and generally include any type of computer network that uses wireless data. Examples of wireless communications networks include, cell phone networks, Wi-Fi networks, Bluetooth®, terrestrial microwave or radio wave networks and the like, for example.

The ergonomic grip (120) is configured to be gripped by a person when walking with the assisted walking device (100). The ergonomic grip (120) may include one more depression that are spatially arranged in a series to be complementary to the grip of a person. In some embodiments, the ergonomic grip (120) may be smooth, rigid or curved, for example. The ergonomic grip (120) may also include padding, gripping, ribs or other structures or materials used to increase the grip and comfort of a person during use of the assisted walking device (100).

The ergonomic grip (120) may be constructed from any type of material that is sufficient to function as described and claimed herein. For example, the ergonomic grip (120) may be constructed from plastics, metals, non-metals, alloys, resins, composite materials, organic compounds, non-organic compounds, papers, fabrics, combinations thereof and the like. The ergonomic grip (120) may be constructed from a unitary piece of material or alternatively may be constructed from a variety of different materials. Further, the shape of the ergonomic grip (120) may be any shape, including but not limited to a circular, square or triangular shape for example. Further, ergonomic grip (120) may include reinforcing or bracing structures, such as ribs or struts, for example, or combinations thereof. The shape of the ergonomic grip (120) is shown as having a substantially linear shape, it being understood however, that the shape of the ergonomic grip (120) may be modified to fit any desired shape, including any desired shape of the handle (105).

As shown therein, the elongated housing (130) includes a top end (135), a bottom end (140) and an opening (145) into an interior chamber (150). The interior chamber (150) extending between the top end (135) and the bottom end (140) of the elongated housing (130). The interior chamber (150) having an upper shelf (155) and a lower shelf (160) positioned therein. The top end (135) of the elongated housing (130) detachably connected to the bottom end (140) of the handle (105).

The interior chamber (150) is configured so that the oxygen concentrator (170), including its component parts, may be secured therein and detachably removed therefrom. The upper shelf (155) and lower shelf (160) are configured to support the oxygen concentrator (170) when positioned therein. It being understood that the oxygen concentrator (170) may be detachably connected thereto by any means known in the art, including, but not limited to, snaps, braces, screws, adhesive, bolts, combinations thereof and the like.

The elongated housing (130) may be constructed from any type of material that is sufficient to function as described and claimed herein. For example, the elongated housing (130) may be constructed from plastics, metals, non-metals, alloys, resins, composite materials, organic compounds, non-organic compounds, papers, fabrics, combinations thereof and the like. The elongated housing (130) may be constructed from a unitary piece of material or alternatively may be constructed from a variety of different materials. The elongated housing (130) may also include reinforcing or bracing structures, such as ribs or struts, for example, or combinations thereof. Further, the shape of the elongated housing (130) may be any shape, including but not limited to a circular, square or triangular shape for example. The shape of the elongated housing (130) is shown as having a substantially circular shape, it being understood however, that the shape of the elongated housing (130) may be modified to fit any desired shape, including any desired shape of the handle (105).

As shown therein, the oxygen concentrator (170) is detachably connected to and positioned within the interior chamber (150) of the elongated housing (130). The oxygen concentrator (170) is secured by the upper shelf (155) and lower shelf (160) of the interior chamber (150). The oxygen concentrator (170) includes an adsorption system (180) configured to generate a flow of oxygen enriched gas, a compressor (185) that includes a motor (190), a plurality of sieve beds (195) configured to extract oxygen-enriched gas from ambient air, a controller (200) in communication with the control pad (110) positioned on the handle (105) and a batter (205). The oxygen concentrator (170) is a medical device configured for delivering doses or a continuous dose or stream of oxygen to a patient in need of additional oxygen. In some embodiments, the oxygen concentrator (170) is configured to be replaceable, such that the oxygen concentrator (170) may be selectively inserted and selectively removed from the assisted walking device (100) through the opening (145) in the elongated housing (130). Further, in some embodiments, the sieve beds (195) and the battery (205) of the oxygen concentrator (170) are configured to be replaceable, such that the sieve beds (195) and the battery (205) may be selectively inserted and selectively removed from the oxygen concentrator (170).

The oxygen concentrator (170) filters the surrounding air, compresses it to the required density and then delivers the concentrated oxygen into a dose delivery system or continuous stream to the patient. The oxygen concentrator (170) may be equipped with special filters and sieve beds, including sieve beds (195) which are filters used to remove nitrogen as well as other contaminants from the air to ensure delivery of purified oxygen to the patient. The oxygen concentrator (170) includes an electronic user interface (the control pad (110)) in communication with the controller (200) so a user can adjust the levels of oxygen concentration and delivery settings directly from the handle (105) of the assisted walking device (100). The concentrated oxygen may then be inhaled by a user through the nasal cannula or a special mask, for example. Oxygen can be delivered in a pulse dose (also called an intermittent flow or on demand flow) or intermittently, usually in milliliters per breath (ml/breath). In some embodiments, the ability to conserve oxygen using the intermittent flow or on demand flow helps to extending battery life and reduce the size and weight of the oxygen concentrator. Continuous flow oxygen is measured in liters per minute (LPM) and may require a larger molecular sieve bed and motor assembly to provide the continuous uninterrupted flow of oxygen. Ambient air passes from the oxygen concentrator, through one or more vents located on the elongated housing (130), and through the molecular sieve beds (195) of zeolite granules, which adsorb the nitrogen. Some of the oxygen produced is delivered to the patient and some is fed back into the sieve beds (195) to further clear them of the accumulated nitrogen, preparing them for the next cycle.

As shown therein, the leg member (209) includes a top end (211) and a bottom end (213). The top end (211) of the leg member (209) detachably connected to the bottom end (213) of the elongated housing. The leg member (209) is configured to be telescopically extendable and retractable so that the assisted walking device (100) may be used with a variety of different sized and shaped people. The leg member (209) may be constructed from any type of material that is sufficient to function as described and claimed herein. For example, the leg member (209) may be constructed from plastics, metals, non-metals, alloys, resins, composite materials, organic compounds, non-organic compounds, papers, fabrics, combinations thereof and the like. The leg member (209) may be constructed from a unitary piece of material or alternatively may be constructed from a variety of different materials. Further, the shape of the leg member (209) may be any shape, including but not limited to a circular, square or triangular shape for example. Further, the leg member (209) may include reinforcing or bracing structures, such as ribs or struts, for example, or combinations thereof. The shape of the leg member (209) is shown as having a substantially circular shape, it being understood however, that the shape of the leg member (209) may be modified to fit any desired shape, including any desired shape of the elongated housing (130).

As shown therein, the foot member (225) is for stabilizing the assisted walking device (100) on a ground surface. The foot member (225) has a top end (230) and a bottom end (235). The top end (230) of the foot member (225) detachably connected to the bottom end (213) of the leg member (209). The bottom end (235) of the foot member (225) for contacting the ground surface. In some embodiments, the assisted walking device (100) includes a single foot member (225) while in other embodiments, the assisted walking device (100) may include a plurality of foot member (225), for example. Each foot member (225) may have a single point of contact or alternatively may have multiple points of contact, including a foot member (225) with three or four points of contact for example. Further, in some embodiments, the foot member (225) may further include support tips detachably connected to the foot member (225), including for example, support tips made from rubber and the like, to grip the ground surface and provide additional support to prevent wear and tear of the leg member (209) and foot member (225) during use, for example. It being understood that the configuration of the foot member (225) may be varied and adjusted to accommodate a variety of different sized and shaped people and depending upon the amount of assistance and stabilization required for each such person.

The foot member (225) may be constructed from any type of material that is sufficient to function as described and claimed herein. For example, the foot member (225) may be constructed from rubber, plastics, metals, non-metals, alloys, resins, composite materials, organic compounds, non-organic compounds, papers, fabrics, combinations thereof and the like. The foot member (225) may be constructed from a unitary piece of material or alternatively may be constructed from a variety of different materials. The foot member (225) may also include reinforcing or bracing structures, such as ribs or struts, for example, or combinations thereof. Further, the shape of the foot member (225) may be any shape, including but not limited to a circular, square or triangular shape for example. The shape of the foot member (225) is shown as having a substantially tri-pod shape, it being understood however, that the shape of the foot member (225) may be modified to fit any desired shape, including any desired shape of the leg member (209) and the elongated housing (130).

Figure 3:
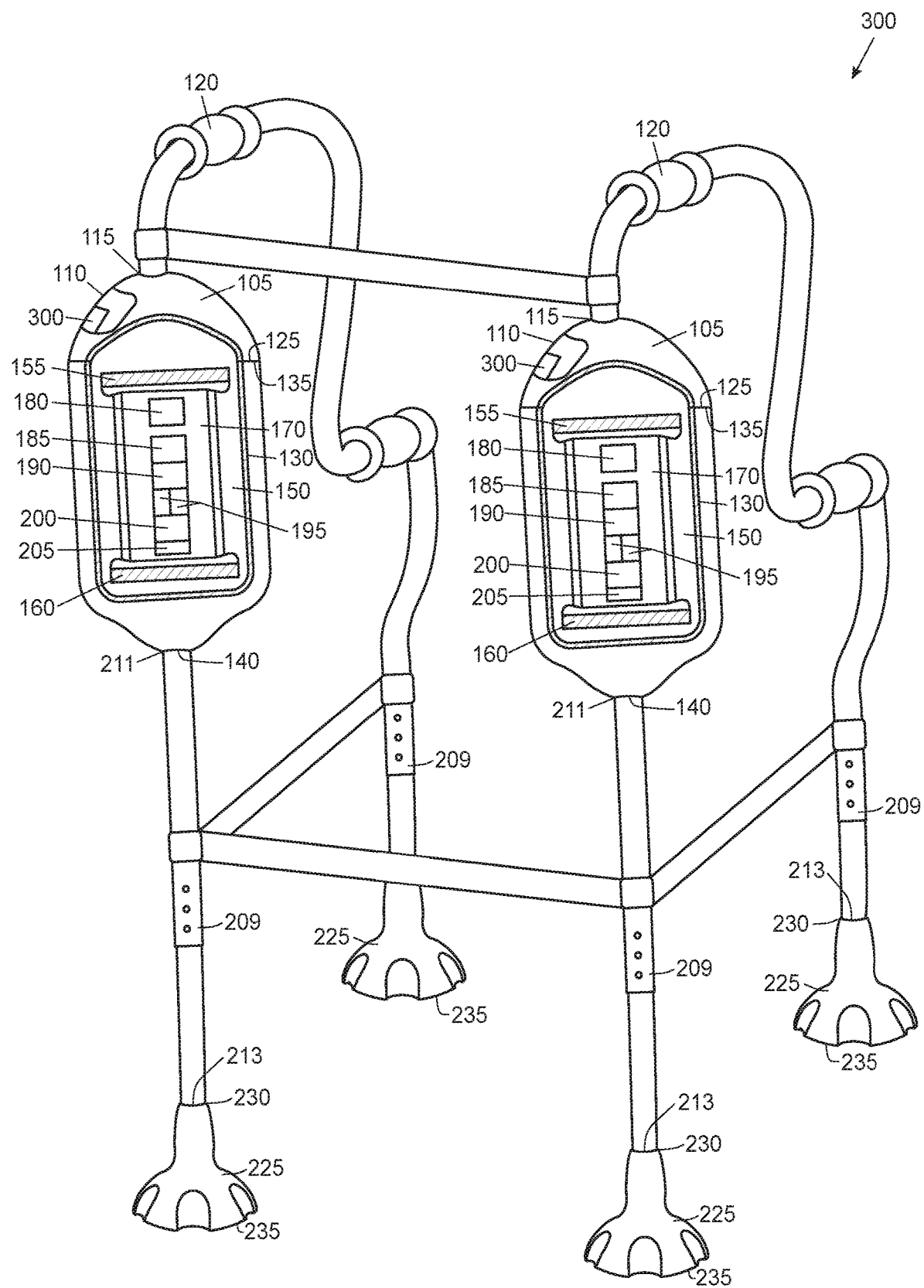
FIG. 3 is a perspective sectional view of an embodiment of an assisted walking device (400) in accordance with the inventive concepts disclosed herein.

Referring now to FIG. 3, shown therein is a perspective sectional view of an embodiment of an assisted walking device (400) in accordance with the inventive concepts disclosed herein. As shown therein, the elongated housing (130) of the assisted walking device includes a plurality of assisted walking devices (100) detachably connected together. The assisted walking device (400) includes a handle (105). The handle (105) having a control pad (110), a top end (115), an ergonomic grip (120), and a bottom end (125). The assisted walking device (400) further including an elongated housing (130). The elongated housing (130) having a top end (135), a bottom end (140), and an opening (145) into an interior chamber (150). The interior chamber (150) extending between the top end (135) and the bottom end (140) of the elongated housing (130). The interior chamber (150) having an upper shelf (155) and a lower shelf (160) positioned therein. The top end (135) of the elongated housing (130) detachably connected to the bottom end (140) of the handle (105).

The assistive walking device (400) further including an oxygen concentrator (170). The oxygen concentrator (170) detachably positioned within the interior chamber (150) of the elongated housing (130) and detachably secured by the upper shelf (155) and lower shelf (160) of the interior chamber (150) of the elongated housing (130). The oxygen concentrator (170) including an adsorption system (180) configured to generate a flow of oxygen enriched gas, a compressor (185) that includes a motor (190), a plurality of sieve beds (195) configured to extract oxygen-enriched gas from ambient air, a controller (200) in communication with the control pad (110) positioned on the handle (105), and a battery (205).

The assisted walking device (400) further includes a leg member (209) for supporting the assisted walking device (400). The leg member (209) having a top end (211) and a bottom end (213). The top end (211) of the leg member (209) detachably connected to the bottom end (140) of the elongated housing (130). The assisted walking device (400) further includes a foot member (225) for stabilizing the assisted walking device (400) on a ground surface. The foot member (225) having a top end (230) and a bottom end (235). The top end (230) of the foot member (225) detachably connected to the bottom end (213) of the leg member (209). The bottom end (235) of the foot member (225) for contacting the ground surface.

The assisted walking device (400) further includes a second handle (105). The handle (105) having a control pad (110), a top end (115), an ergonomic grip (120), and a bottom end (125). The assisted walking device (400) further including a second elongated housing (130). The elongated housing (130) having a top end (135), a bottom end (140), and an opening (145) into an interior chamber (150). The interior chamber (150) extending between the top end (135) and the bottom end (140) of the elongated housing (130). The interior chamber (150) having an upper shelf (155) and a lower shelf (160) positioned therein. The top end (135) of the elongated housing (130) detachably connected to the bottom end (140) of the handle (105).

The assistive walking device (400) further including a second oxygen concentrator (170). The oxygen concentrator (170) detachably positioned within the interior chamber (150) of the elongated housing (130) and detachably secured by the upper shelf (155) and lower shelf (160) of the interior chamber (150) of the elongated housing (130). The oxygen concentrator (170) including an adsorption system (180) configured to generate a flow of oxygen enriched gas, a compressor (185) that includes a motor (190), a plurality of sieve beds (195) configured to extract oxygen-enriched gas from ambient air, a controller (200) in communication with the control pad (110) positioned on the handle (105), and a battery (205).

The assisted walking device (400) further includes a second leg member (209) for supporting the assisted walking device (100). The leg member (209) having a top end (211) and a bottom end (213). The top end (211) of the leg member (209) detachably connected to the bottom end (140) of the elongated housing (130). The assisted walking device (400) further includes a second foot member (225) for stabilizing the assisted walking device (100) on a ground surface. The foot member (225) having a top end (230) and a bottom end (235). The top end (230) of the foot member (225) detachably connected to the bottom end (213) of the leg member (209). The bottom end (235) of the foot member (225) for contacting the ground surface.

The assisted walking device (400) may be constructed similarly to and operated similarly to the assisted walking device (100) described above. For example, the assisted walking device (400) may be constructed from any type of material that is sufficient to function as described and claimed herein. For example, the assisted walking device (400) may be constructed from plastics, metals, non-metals, alloys, resins, composite materials, organic compounds, non-organic compounds, papers, fabrics, combinations thereof and the like. The assisted walking device (400) may be constructed from a unitary piece of material or alternatively may be constructed from a variety of different materials. The assisted walking device (400) may also include reinforcing or bracing structures, such as ribs or struts, for example, or combinations thereof. Further, the shape of the assisted walking device (400) may be any shape, including but not limited to a circular, square or triangular shape for example and each component part of the assisted walking device (400) may be detachably connected by any means known in the art. For example, screws, snaps, pins, bolts, combinations thereof and the like.

It is to be appreciated that embodiments of the assisted walking device (100) and embodiments of the assisted walking device (400) may be used under a variety of different conditions and embodied within a variety of different assisted walking devices. Including, but not limited to a cane, a walker, and a wheelchair, for example. Further, embodiments of the assisted walking device (100) and assisted walking device (400) may be shipped fully assembled, fully or partially disassembled as will be readily appreciated by persons of ordinary skill in the art.

From the above description, it is clear that the inventive concepts disclosed herein are adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the broad scope of the inventive concepts disclosed herein and defined by the appended claims.

What is claimed is:

1. A therapeutic assisted walking device comprising:
   a handle having a top end, an ergonomic grip, and a bottom end;
   a control pad connected to the handle, the control pad comprising a touch screen and one or more computers for transmitting, receiving, storing, and recording real time data associated with the health of the user and transmitting the data to one or more remote computers to monitor, track progress, and provide treatment and therapy for the user based on the real time health data associated with the user recorded by the control pad and transmitted to the one or more remote computer;
   an elongated housing, the elongated housing having a top end, a bottom end, and an opening into an interior chamber, the interior chamber extending between the top end and the bottom end of the elongated housing, the interior chamber having an upper shelf and a lower shelf positioned therein, the top end of the elongated housing detachably and directly connected to the bottom end of the handle;
   an integrated oxygen concentrator, the oxygen concentrator disposed within the elongated housing, the oxygen concentrator detachably positioned within the interior chamber of the elongated housing and detachably secured by the upper shelf and lower shelf of the interior chamber of the elongated housing, the oxygen concentrator comprising an adsorption system configured to generate a flow of oxygen enriched gas, a compressor that comprises a motor, a plurality of sieve beds configured to extract oxygen-enriched gas from ambient air, a controller in communication with the control pad positioned on the handle, and a battery;
   a leg member for supporting the assisted walking device, the leg member detachably connected to the elongated housing and positioned directly below the bottom end of the elongated housing to enable a natural walking gait for the user when using the assisted walking device, the leg member having a top end and a bottom end, the top end of the leg member detachably connected to the bottom end of the elongated housing; and
   a foot member for stabilizing the assisted walking device on a ground surface, the foot member having a top end and a bottom end, the top end of the foot member detachably connected to the bottom end of the leg member, the bottom end of the foot member for contacting the ground surface.

2. The therapeutic assisted walking device of claim 1 wherein the oxygen concentrator is configured to be replaceable, such that the oxygen concentrator may be selectively inserted and selectively removed from the assisted walking device through the opening in the elongated housing.

3. The therapeutic assisted walking device of claim 1 wherein the sieve beds and the battery of the oxygen concentrator are configured to be replaceable, such that the sieve beds and the battery may be selectively inserted and selectively removed from the oxygen concentrator.

4. The therapeutic assisted walking device of claim 1 wherein the foot member further includes one or more wheels connected thereto.

5. The therapeutic assisted walking device of claim 1 further comprising a second leg member; a third leg member, and a fourth leg member, arranged in a square configuration, wherein each of the second, third and fourth leg member is detachably connected to the elongated housing.

* * * * *